(12) United States Patent
Kolar et al.

(10) Patent No.: US 10,376,216 B2
(45) Date of Patent: Aug. 13, 2019

(54) DEVICE FOR CONTACTLESS MONITORING OF PATIENT'S VITAL SIGNS

(71) Applicant: LINET SPOL. S R.O., Slany (CZ)

(72) Inventors: Vladimir Kolar, Slany (CZ); Libor Seidl, Beroun (CZ)

(73) Assignee: LINET SPOL. S R.O., Slany (CZ)

( * ) Notice: Subject to any disclaimer, the term of this patent is extended or adjusted under 35 U.S.C. 154(b) by 248 days.

(21) Appl. No.: 15/027,211

(22) PCT Filed: Oct. 8, 2014

(86) PCT No.: PCT/CZ2014/000112
§ 371 (c)(1),
(2) Date: Apr. 4, 2016

(87) PCT Pub. No.: WO2015/051770
PCT Pub. Date: Apr. 16, 2015

(65) Prior Publication Data
US 2016/0235367 A1    Aug. 18, 2016

(30) Foreign Application Priority Data

Oct. 8, 2013  (CZ) .................................. 2013-781

(51) Int. Cl.
*A61B 5/08*  (2006.01)
*A61B 5/00*  (2006.01)
(Continued)

(52) U.S. Cl.
CPC .......... *A61B 5/6892* (2013.01); *A61B 5/0205* (2013.01); *A61B 5/0245* (2013.01);
(Continued)

(58) Field of Classification Search
CPC ................ A61B 5/0816; A61B 5/6892; A61B 2562/0247; A61B 5/1115
See application file for complete search history.

(56) References Cited

U.S. PATENT DOCUMENTS 5,448,996 A * 9/1995 Bellin .................. A61B 5/0205
600/534
2003/0115966 A1  6/2003 Ueno
(Continued)

FOREIGN PATENT DOCUMENTS

EP  1 837 638 A1   9/2007
JP  2004226294 A *  8/2004
(Continued)

OTHER PUBLICATIONS

WIPO, European Patent Office, International Search Report, in International Application No. PCT/CZ2014/000112 filed Oct. 8, 2014, dated Dec. 5, 2014.
(Continued)

*Primary Examiner* — Eric J Messersmith
(74) *Attorney, Agent, or Firm* — Thedford I. Hitaffer; Hitaffer & Hitaffer, PLLC

(57) ABSTRACT

Device for contactless monitoring of a patient's vital signs in the form of a measuring mat comprising at least one measuring element. The measuring element comprises a piezoelectric sensor with a first and a second conductive electrode and a piezoelectric element. Near the piezoelectric sensor is a third conductive electrode. The exertion of a mechanical force on the cover of the measuring element results in a change in the distance between at least one of the electrodes of the piezoelectric sensor and the third conductive electrode. This change in distance is expressed as a difference in the detected parameter corresponding to a change in the patient's vital signs.

12 Claims, 4 Drawing Sheets

(51) Int. Cl.
  *A61B 5/0205*  (2006.01)
  *A61B 5/024*   (2006.01)
  *A61B 5/0245*  (2006.01)
  *A61B 5/11*    (2006.01)
  *A61B 5/113*   (2006.01)
(52) U.S. Cl.
  CPC ........ *A61B 5/02444* (2013.01); *A61B 5/0816* (2013.01); *A61B 5/113* (2013.01); *A61B 5/1115* (2013.01); *A61B 2562/0247* (2013.01); *A61B 2562/043* (2013.01); *A61B 2562/046* (2013.01)

(56) References Cited

U.S. PATENT DOCUMENTS

2008/0269625 A1\* 10/2008 Halperin ................ A61B 5/113
                                                              600/508
2011/0040206 A1    2/2011 Burger
2012/0180567 A1    7/2012 Koyama

FOREIGN PATENT DOCUMENTS

TW    201 023 827 A   7/2010
WO    00/05771 A1     2/2000

OTHER PUBLICATIONS

WIPO, European Patent Office, Written Opinion of the International Searching Authority, in International Application No. PCT/CZ2014/000112 filed Oct. 8, 2014, dated Dec. 5, 2014.
WIPO, European Patent Office, International Preliminary Report on Patentability, in International Application No. PCT/CZ2014/000112 filed Oct. 8, 2014, dated Feb. 10, 2016.

\* cited by examiner

ована mnoha výzkumy...

DEVICE FOR CONTACTLESS MONITORING OF PATIENT'S VITAL SIGNS

CROSS-REFERENCE TO RELATED APPLICATIONS

This application, filed under 35 USC 371, is a United States National Stage Application of International Application No. PCT/CZ2014/000112, filed Oct. 8, 2014, which claims priority to CZ Application No. PV 2013-781, filed on Oct. 8, 2013, the disclosures of which are incorporated herein by reference.

TECHNICAL FIELD

The invention is a device for monitoring a patient's vital signs. The patient's respiratory and pulse rate is measured using a measuring mat with one or more built-in measuring members. Each of these measuring members consists of a unique sensor which senses the mechanical action of forces on the mat resulting from the patient's breathing and pulse.

TECHNICAL BACKGROUND

Current art offers a great number of devices for monitoring a patient's vital signs. These monitors are regularly used in many hospitals, primarily in intensive care units. Thanks to modern technologies a patient doesn't have to be connected to a device by any cables and there is no longer a necessity of a patient and hospital personnel to cooperate for the successful monitoring of the patient's vital signs. These contactless monitoring systems can also be used in aftercare departments or nursing homes.

Most of these modern, but no longer overly unique, devices are based on a similar principle. The main component of the measuring device is a mat with one or more integrated sensors. These sensors may be of different types. One of the types is a sensor which senses changes in forces acting on the mat. Another method uses accelerometers measuring the vibrations of the mattress platform in order to measure vital signs. It is also possible to use, for example, piezoelectric sensors and also additional capacitive sensors. The mat is located under the location where the patient is recumbent generally under the mattress.

Many embodiments of mats are known, i.e. in patent application WO 2010080794 the mat is filled with a fluid and a pressure sensor senses changes in pressure caused by the patient's breath and pulse rate. The problem of the solution is the complexity of manufacturing a special mat filled with fluid.

One interesting solution is an evaluation of vital signs on the basis of an analysis of video signal. Some vital signs are calculated on the basis of the ratio of the intensity of light of two different wavelengths reflected from the patient's skin. Such a solution is described for example in patent application WO 2013027027. But this method is not very accurate and it is also difficult to make a measurement using this method under poor lighting conditions.

There are also known solutions where the measuring member is integrated in the mattress. We can see such a solution for example in U.S. Pat. No. 7,652,581. One disadvantage may be the price of the mattress adapted for this purpose.

Strain gauges, the main role of which is evaluation of a patient's weight, may also be used for the implementation of a measuring device. If they are correctly adapted they can also record the vibrations caused by breathing and heartbeat. But highly sensitive strain gauges are necessary for this method of measurement and they may be prone to interference and can often react to ambient forces which are not a subject of interest. We can see such a solution in U.S. Pat. No. 7,699,784.

As a result of the drop in the purchasing price of piezoelectric sensors they are used in many branches, from medical devices, uses in the army or for building security. Piezoelectric sensors are used in medical devices, for example in plethysmography, measuring of blood pressure, measuring tremors, the movement of a patient or measuring the pulse rate. Piezoelectric sensors work on the principle that they react to deformation by generating measurable electrical voltage. They can be used to measure force, flexion, extension and other values. The problem is that a piezoelectric sensor reacts very badly to low frequency changes such as respiratory frequency. We can find the use of these piezoelectric sensors for contactless monitoring of vital signs in U.S. Pat. No. 6,984,207, for example.

Capacitive sensors are often a part of medical equipment, and their advantage is that compared to piezoelectric sensors they are also sensitive to low frequency mechanical changes which are result of applied forces. For this reason they have a wide range of uses, from measuring the level of liquid, measuring position or measuring force, which can be used to measure a patient's respiration, for example. The use of these capacitive sensors is described for example in patent application WO 2006131855.

Contactless measurement of a patient's vital signs may be performed using inductive sensors that measure the bio-impedance of the patient, on the basis of which the patient's physiological expressions are evaluated. Such an embodiment is given, for example, in patent application WO 2006129212.

A modern trend in medicine is lower intervention in the patient's daily activities and so contactless measurement of the patient's vital signs is more attractive. Most often embodiment of the present measurement of vital signs is a mat consisting of one or more types of sensors. The sensors are for example piezoelectric, pressure or capacitive sensors. These sensors differ in terms of their ability to react to mechanical changes resulting from the patient's vital signs. For example a piezoelectric sensor is distinguished by the fact that it reacts well to dynamic changes which can be caused for example by the patient's pulse. Capacitive sensors react well to slow changes such as a patient's respiration. The problem given by making contactless equipment for the measurement of a patient's vital signs is that the sensors must be sensitive to even slight changes caused mainly by the breathing and pulse of the patient and they must not be disrupted by ambient forces. This can be achieved through a combination of different types of sensors but it leads to very expensive measuring devices.

SUMMARY OF INVENTION

Mentioned problems are resolved by a device for contactless monitoring of the patient's vital signs including a measuring mat including one or more measuring members. One part of the measuring member is a piezoelectric sensor including a first and a second conductive electrode and a piezoelectric element. This is a unique solution because it contains a third conductive electrode proximate to the piezoelectric sensor. If the mechanical force is applied on the cover of the measuring member the distance between at least one of the electrodes of the piezoelectric sensor and the third conductive electrode changes. This solution is advantageous because only one type of a measuring element modified in this way is used for the contactless monitoring of the patient's vital signs.

Application of a mechanical force on the cover caused by the patient's vital signs results the deflection of a metal strip. The arrangement of the metal strip, cover and supporting body is approximately symmetrical, which means that the same perpendicular force can exert anywhere on the entire surface of the cover, and it is expressed as the same deflection of the metal strip. In an advantageous embodiment the measuring member includes a flexible member which exerts a mechanical force on the piezoelectric sensor via in the direction to the metal strip. An alternative embodiment contains the piezoelectric sensor mechanically fixed to the metal strip.

In an advantageous embodiment the device for contactless monitoring of a patient's vital signs is able to measure the change in position or presence of a patient.

BRIEF DESCRIPTION OF DRAWINGS

The measuring mat is shown in FIG. 1. FIG. 4 contains a close-up of the circuit board including piezoelectric sensor. A cross-section through the measuring element in the position where no force is acting on the measuring element is shown in FIG. 5, whereas

DETAILED DESCRIPTION OF DRAWINGS

Figure 1:
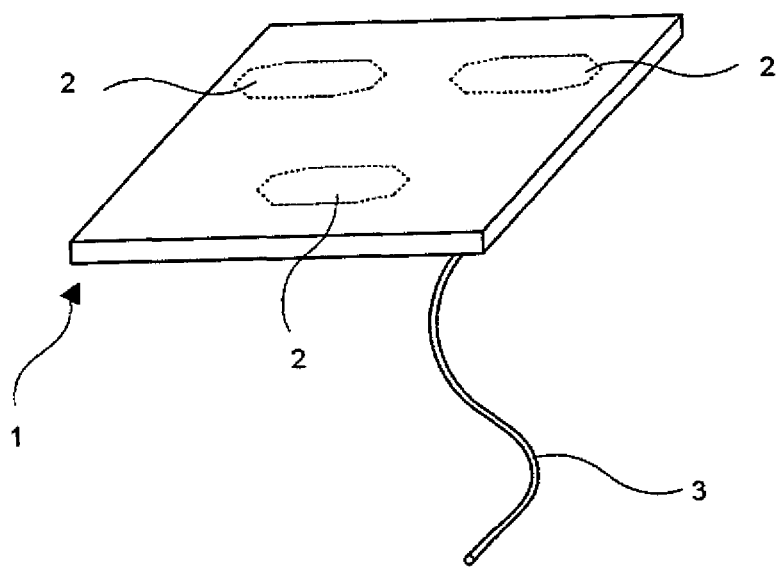
Figure 2:
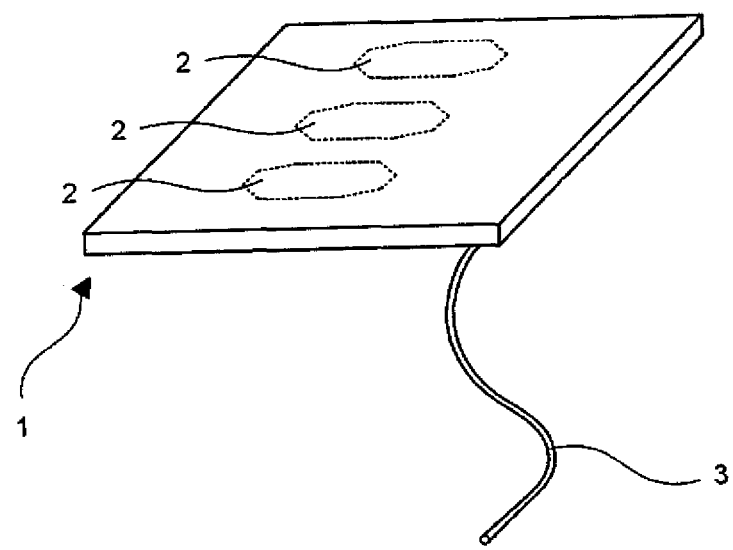
FIG. 2 shows the measuring mat in another preferred embodiment in terms of the arrangement of measuring members.

FIG. 1 and FIG. 2 show two different embodiments of the measuring mat 1 for contactless measurement of a patient's vital signs. Using this measuring mat 1 it is possible to perform contactless measurement of a patient's vital signs. The mat 1 can be inserted between the patient support of a bed and the mattress, in an armchair, a chair or between any backrest and patient's body. The measuring mat 1 may be adapted in both ways by changing its dimensions and the layout of measuring members 2. One part of the measuring mat 1 is a cable 3 for power supply or signal transmission. This cable 3 may also be adapted for data communication and the measuring mat 1 may also be expanded to include a module for wi-fi, Bluetooth® or other means of wireless communication for data communication. For easy handling and cleaning the measuring mat 1 cover is made of flexible waterproof material such as Gore-Tex® textile, plastic sheeting or other light, waterproof materials.

Figure 3:
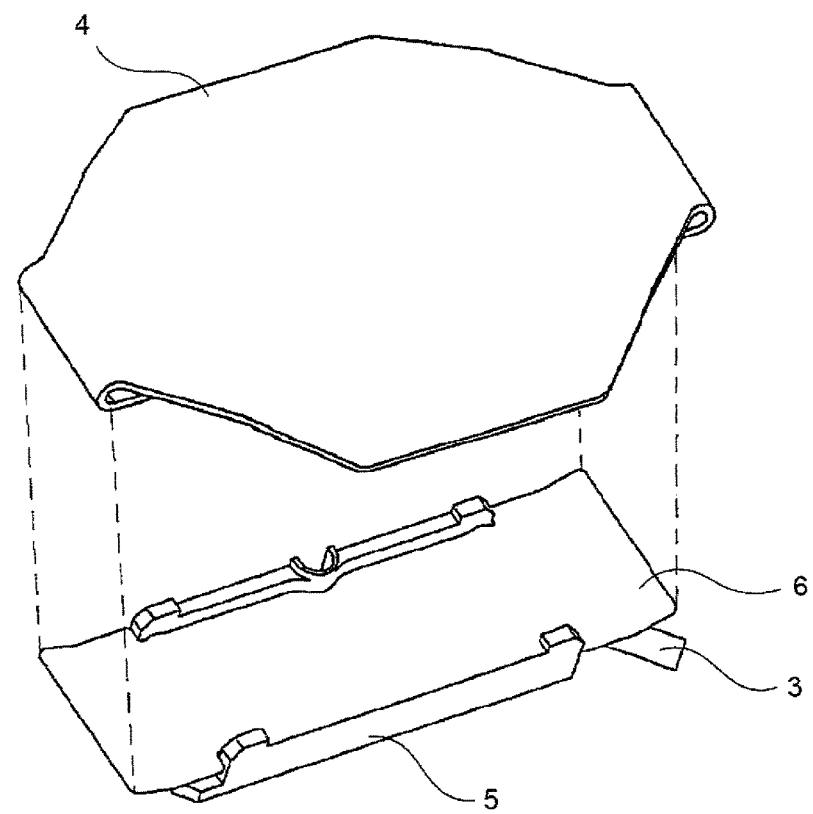
FIG. 3 shows the measuring member, including cover.

FIG. 3 shows a measuring member 2 including a cover 4, supporting body 5 and metal strip 6 against which a piezoelectric sensor 7 is pressed from below. The metal strip 6 flexes when a vertical force is applied on the cover 4. The supporting body 5 is shaped so that the metal strip 6 fits precisely into part of the supporting body 5 and also so that there is protection for the main part of the measuring member 2 including the sensor for monitoring slow changes, for example a capacitive sensor 8 and sensor for monitoring rapid changes, for example a piezoelectric sensor 7. The cover 4 presses in several places against the metal strip 6 and in this way it transfers to the metal strip 6 the force applied on it from the surroundings. One part of the measuring member 2 is a cable 3 serving for example for power supply and signal transfer.

Figure 4:
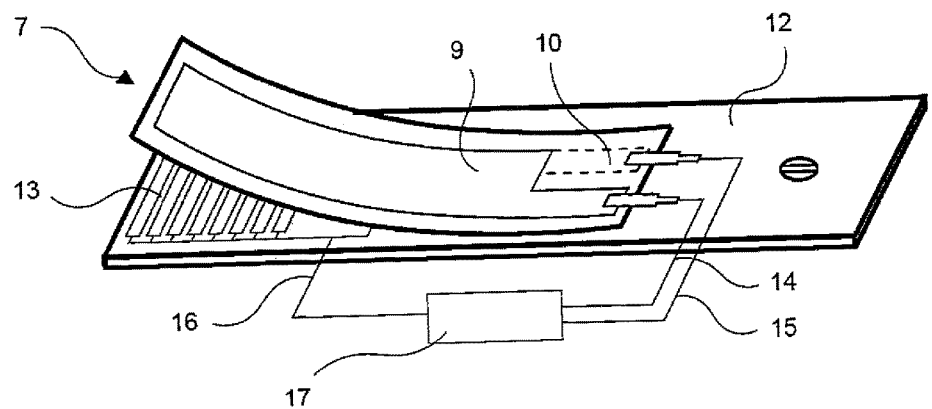

FIG. 4 shows a piezoelectric sensor 7 including a first conductive electrode 9 and a second conductive electrode 10. An piezoelectric element (not in figure) is placed between these conductive electrodes 9, 10. The construction of such piezoelectric sensors 7 is generally known, one example may be the DT Series piezoelectric sensor 7 made by the company Measurement Specialties. The piezoelectric sensor 7 attached to a circuit board, for example a printed circuit board 12. One part of the printed circuit board 12 is a third conductive electrode 13 near the piezoelectric sensor 7. Along with one of the conductive electrodes 9, 10 of the piezoelectric sensor 7 the third conductive electrode 13 forms a capacitor the parameters of which change depending on the distance between at least one of the conductive electrodes 9, 10 of the piezoelectric sensor 7 and third conductive electrode 13. First conductor 14, second conductor 15 and third conductor 16 serve to connect the electrodes 9, 10, 13 with the processing unit 17.

Figure 5:
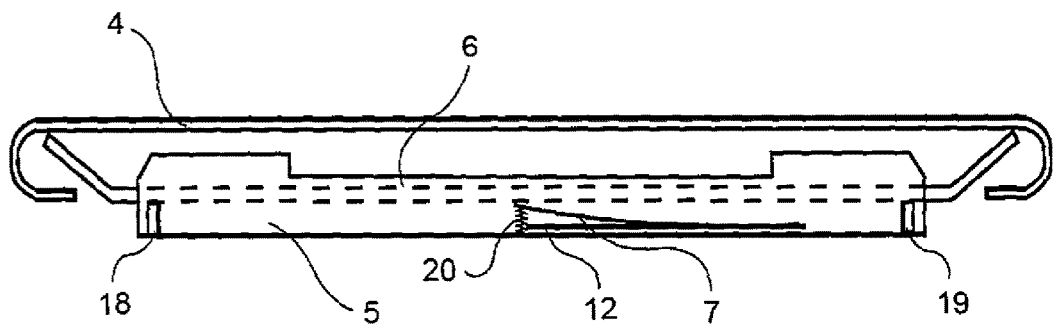

FIG. 5 to FIG. 8 show a detailed description of the principle according to the invention. FIG. 5 shows a cross-section of the measuring member 2 in the first position, where no external force is applied on the cover 4. It shows the cover 4, supporting body 5 of the measuring element, metal strip 6, first rail 18 and second rail 19, which the metal strip 6 is put on. The piezoelectric sensor 7 presses against approximately the centre of the metal strip 6 and is connected at the other end to the circuit board 12. One part of the measuring member 2, as in FIG. 5, may be a flexible member 20 which interacts with the piezoelectric sensor 7 via a force in the direction to the metal strip 6. This flexible member 20 may be a spring. In an alternative embodiment the piezoelectric sensor is fixed to the metal strip 6 and a spring doesn't have to be a part of the measuring member 2.

Figure 6:
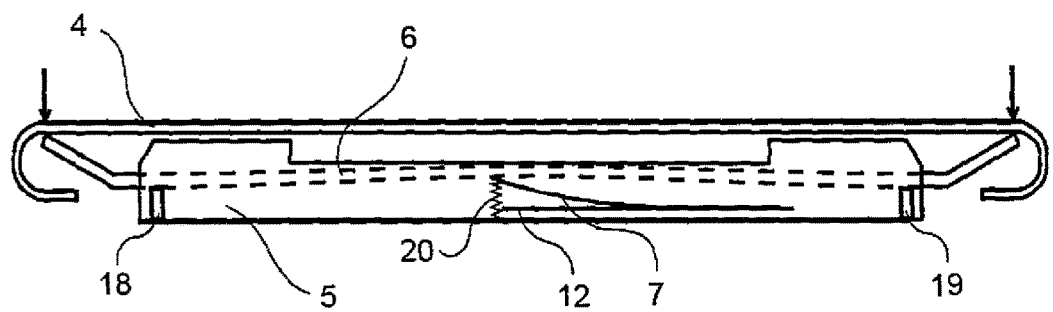
FIG. 6 shows a cross-section of the measuring element where a perpendicular force is acting on the cover.

FIG. 6 shows a cross-section of the measuring member 2 subjected to a perpendicular force on the cover 4. The transmission of this perpendicular force independent of the place of exerting occurs via two points of contact between the cover 4 and the metal strip 6. So the applying of a perpendicular force on the cover 4 expressed by a deflection of the metal strip 6 at a place near the piezoelectric sensor 7 from its original position. The fact that the technical arrangement of the metal strip 6, cover 4 and supporting body 5 is approximately symmetrical means that the same perpendicular force can act anywhere on the entire surface of the cover 4 it is expressed as the same deflection of the metal strip 6.

Figure 7:
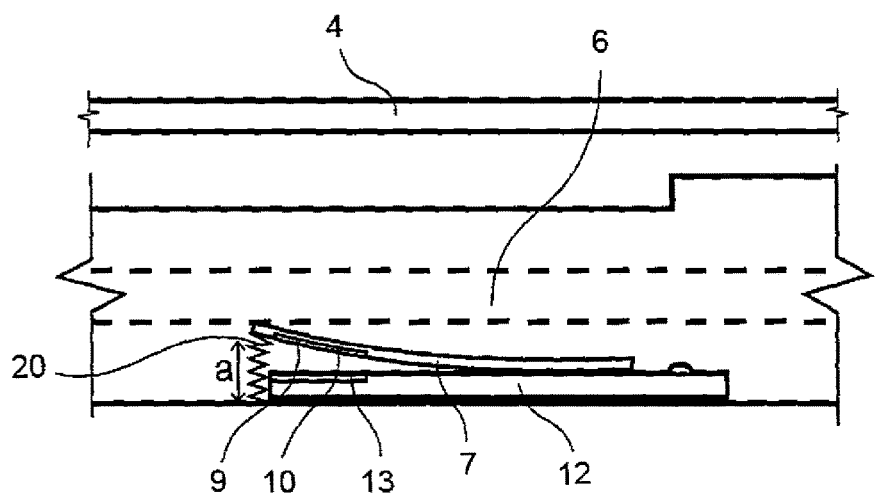
FIG. 7 shows a close-up of a cross-section of the measuring element at the place of the piezoelectric sensor.
Figure 8:
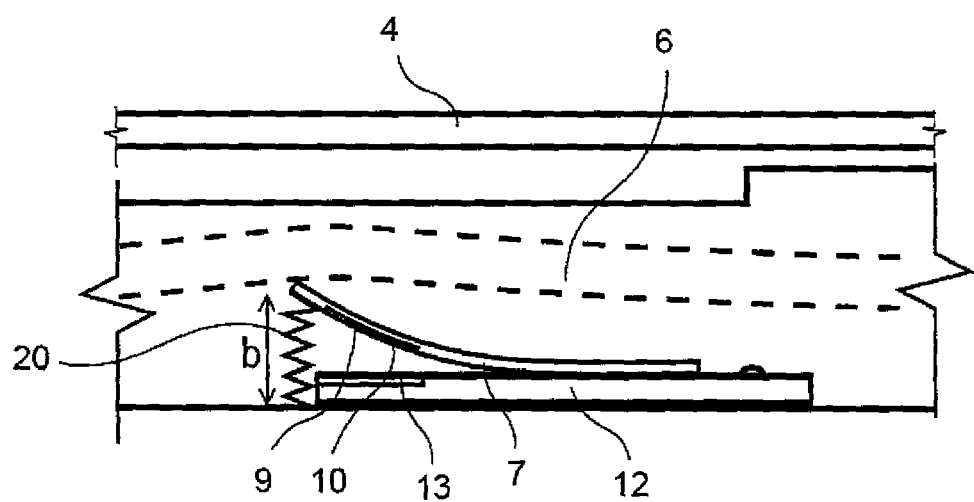
FIG. 8 shows a close-up of a cross-section of the measuring element at the place of the piezoelectric sensor when a perpendicular force is acting.

FIG. 7 and FIG. 8 show how the action of a perpendicular force is expressed on a piezoelectric sensor 7 itself. FIG. 7 shows a section of the central part of the measuring member 2. In FIG. 6 the measuring member 2 is shown with the circuit board 12 and with the piezoelectric sensor 7 in the first position where no external force exerts on the cover. FIG. 8 shows this part of the measuring member 2 with applied perpendicular force on the cover 4. If the perpendicular force acts on the cover 4 the metal strip deflects from its first position in the direction away from the supporting body 5. Since the piezoelectric sensor 7 is pushed by the flexible member 20 against the metal strip 6, during the deflection of the metal strip 6 the piezoelectric sensor 7 moves with it. The distance between at least one of the conductive electrodes 9, 10 on the piezoelectric sensor 7 and the third conductive electrode 13 increases, which results in a drop in the measured capacity. An ordinary expert skilled in the art is capable of designing an alternative solution where the application of a perpendicular force on the cover 4 causes the metal strip 6 to deflect in the direction to the supporting body 5 of the measuring member 2. Hence the distance between at least one of the conductive electrodes 9, 10 on the piezoelectric sensor 7 and the third conductive electrode 13 will decrease and this increases the measured capacity.

The application of the perpendicular force on the cover 4 causes a deformation of the piezoelectric sensor 7, which generates a voltage between the first conductor 14 and the second conductor 15. This method of measuring reacts to rapidly caused changes, for example, by the patient's pulse. The deflection of the piezoelectric sensor 7 causes a change in distance between one of the conductive electrodes 9, 10 of the piezoelectric sensor 7 and the third conductive electrode 13 from distance a to distance b. It results in a change of capacitance of the formed capacitor measured between one of the conductive electrodes 9, 10 of the piezoelectric sensor and the third conductive electrode 13. This second method of measuring senses with great accuracy small changes caused by mechanical expressions of the patient's body. Low frequency changes in capacity correspond, for example, to respiratory rate where a sudden and significant increase or decrease in capacity may be evaluated as a change of the patient's presence, i.e., whether or not the patient is in bed. The region of interest for the evaluation of the respiratory rate or increase in weight is the frequency spectrum of changes lower than 1 Hz. A signal with a frequency of 0.2 Hz may be evaluated as the respiratory rate. In contrast, the region of interest for evaluation of the pulse rate is the frequency spectrum of changes around 1 Hz and higher, the pulse rate may be detected up to 10 Hz.

Based on an appropriate layout of measuring members 2 in the mat 1, the processing unit 17 can give information about the patient's position, and if there is a danger that the patient will fall out of bed, it can inform the personnel by signalling a risk of the patient exiting the bed or the patient falling from the bed. This signalling may be visual, audio or in some other form. The signalling can also have a local or system scope, where the risk information is sent by the processing unit 17 to a server, from where the information is distributed to remote devices such as a monitor in a nurse station or a mobile device with which a nurse is equipped. The stopping of measurement may be another reason why to evaluate the risk of exiting the bed.

On the basis of the measurement of slow changes in capacity, in an advantageous embodiment the processing unit 17 can be configured so that it measures the patient's weight and can give information about a reduction or increase in the patient's weight in the case of long-term monitoring.

1 mat
2 measuring member
3 cable
4 cover
5 supporting body
6 metal strip
7 piezoelectric sensor
8 capacitance sensor
9 first conductive electrode
10 second conductive electrode
11 circuit board
12 third conductive electrode
13 first conductor
14 second conductor
15 third conductor
16 processing unit
17 first rail
18 second rail
19 flexible member

The invention claimed is:

1. Device for contactless monitoring of a patient's vital signs, the device comprising:
   a measuring mat,
   a processing unit, and
   at least one measuring member arranged on the measuring mat, the measuring member comprising:
      a cover,
      a metal strip supported in relation to the cover for transmission of a force acting on the cover through the metal strip,
      a piezoelectric sensor pressing against the metal strip opposite the cover, the piezoelectric sensor comprising a first and second conductive electrode and a piezoelectric element, and
      a third conductive electrode connected to the processing unit and placed near the piezoelectric sensor, wherein at least one of the first and second conductive electrodes forms a capacitor in combination with the third conductive electrode, where upon applying the force to the cover, the cover presses against the metal strip, which in turn presses against the piezoelectric sensor to vary a distance between the at least one of the first and second electrodes of the piezoelectric sensor and the third electrode, where the distance varies depending on the force applied, and wherein a change in the distance between the at least one of the first and second electrodes of the piezoelectric sensor and the third electrode is proportional to a change in measured capacitance between the at least one of the first and second electrodes and the third electrode, the capacitance being measured by the processing unit.

2. Device for contactless monitoring of a patient's vital signs according to claim 1 wherein repetitious changes in the capacitance correspond to a change in a patient's respiratory rate.

3. Device for contactless monitoring of a patient's vital signs according to claim 1 wherein a significant change in capacitance of a sensor corresponds to a presence or position of a patient.

4. Device for contactless monitoring of a patient's vital signs according to claim 1 wherein repetitious changes in voltage generated by the piezoelectric sensor correspond to a patient's pulse rate.

5. Device for contactless monitoring of a patient's vital signs according to claim 1 wherein the metal strip, the piezoelectric sensor and the third electrode fit within at least a part of a supporting body, and wherein the metal strip has opposing ends that extend beyond the supporting body to contact a surface of the cover opposite of which the force is applied.

6. Device for contactless monitoring of a patient's vital signs according to claim 5 wherein the piezoelectric sensor is attached to a circuit board fit within at least a part of a supporting body.

7. Device for contactless monitoring of a patient's vital signs according to claim 5, wherein an arrangement of the cover, the metal strip and the supporting body is approximately symmetrical according to at least one plane perpendicular to a longitudinal direction of the measuring member.

8. Device for contactless monitoring of a patient's vital signs according to claim 1 wherein the at least one measuring member is one of at least two measuring members.

9. Device for contactless monitoring of a patient's vital signs according to claim 5 wherein the piezoelectric sensor is pushed against the metal strip by a resilient member.

10. Device for contactless monitoring of a patient's vital signs according to claim 5 wherein the piezoelectric sensor is firmly fixed to the metal strip.

11. Method for contactless monitoring of a patient's vital signs comprising the steps of:
   a) providing a processing unit,
   b) providing a measuring mat having a measuring element comprising:
      a cover,
      a metal strip supported in relation to the cover for transmission of a force acting on the cover through the metal strip,
      a piezoelectric sensor pressing against the metal strip opposite the cover, the piezoelectric sensor comprising a first and second conductive electrode and a piezoelectric element, and
      a third conductive electrode,
   c) connecting the measuring element to the processing unit, and
   d) applying the force to the cover so that the cover presses against the metal strip, which in turn presses against the piezoelectric sensor, that results in a change to a distance between at least one of the first and second conductive electrode of the piezoelectric sensor and the third conductive electrode proximate to the piezoelectric sensor, the distance being proportional to a capacity measured between the at least one of the first and second conducting electrodes and the third conductive electrode by the processing unit.

12. Device for contactless monitoring of a patient's vital signs, comprising:
   a patient support,
   a mattress supported by the patient support,
   a processing unit supported by the patient support, and
   a measuring mat for insertion between the patient support and the mattress,
   at least one measuring member arranged on the measuring mat, the measuring member comprising:
      a cover,
      a metal strip supported in relation to the cover for transmission of force acting on the cover through the metal strip,
      a piezoelectric sensor pressing against the metal strip opposite the cover, the piezoelectric sensor comprising a first and second conductive electrode and a piezoelectric element, and
      a third conductive electrode connected to the processing unit and placed near the piezoelectric sensor, wherein at least one of the first and second conductive electrodes form a capacitor in combination with the third conductive electrode, where upon applying a force to the cover, the cover presses against the metal strip, which in turn presses against the piezoelectric sensor to vary a distance between at least one of the first and second electrodes of the piezoelectric sensor and the third electrode, where the distance varies depending on the force applied, and wherein a change in the distance between the at least one of the first and second electrodes of the piezoelectric sensor and the third electrode is proportional to a change in measured capacitance between the at least one of the first and second electrodes and the third electrode, the capacitance being measured by the processing unit.

* * * * *